United States Patent [19]

Panzer et al.

[11] 4,138,563

[45] Feb. 6, 1979

[54] 2-ACYLAMIDOETHYL-2-TETRAHYDROPYRIMIDINES

[75] Inventors: Hans P. Panzer, Stamford; Kenny U. Acholonu, Bridgeport, both of Conn.

[73] Assignee: American Cyanamid Company, Stamford, Conn.

[21] Appl. No.: 867,250

[22] Filed: Jan. 5, 1978

[51] Int. Cl.$^2$ ............................................. C07D 239/06
[52] U.S. Cl. ...................................... 544/335; 544/242
[58] Field of Search ................. 260/256.4 H; 544/335

[56] References Cited

U.S. PATENT DOCUMENTS 3,278,374   4/1978   Sims et al. ................. 260/256.4 H Primary Examiner—Paul M. Coughlan, Jr.
Attorney, Agent, or Firm—William J. van Loo

[57] ABSTRACT

2-acylamidoethyl-2-tetrahydropyrimidines are disclosed which are desirable precursors for 2-vinyl-2-tetrahydropyrimidines.

5 Claims, No Drawings

2-ACYLAMIDOETHYL-2-TETRAHYDROPYRIMIDINES

CROSS-REFERENCE TO RELATED APPLICATIONS

This application is related to applications Ser. No. 867,249, now abandoned, and 867,065, filed on even date herewith. The instant application relates to 2-acylamidoethyl-2-tetrahydropyrimidines. Ser. No. 867,249 relates to a process for preparation thereof and Ser. No. 867,065 relates to a process for preparing 2-vinyl-2-tetrahydropyrimidines by cleavage of 2-acylamido-2-tetrahydropyrimidines.

This invention relates to precursors useful for preparing vinyl-2-tetrahydropyrimidines. More particularly, this invention relates to 2-acylamidoethyl-2-tetrahydropyrimidines.

The need for high-efficiency products for use in the treatment of aqueous suspensions of solids has continued to grow in recent years because of the increasing awareness of the environment pollution caused by such substances and other considerations. Accordingly, there have been increased efforts expended in attempts to provide such products which can be used to facilitate the dewatering of aqueous suspensions of organic, or mixtures of organic and inorganic, materials such as distillery wastes, fermentation wastes, wastes from paper manufacturing plants, dye plant wastes and sewage suspensions such as digested sludges, activated sludges or raw and primary sludges from sewage treatment plants as well as a host of other suspension types.

The more recent and more successful materials used in the treatment of such suspensions have been amidine or imidazoline polymers, see U.S. Pat. Nos. 3,406,139; 3,450,646; 3,576,740 and 3,666,705. Such polymers are very effective materials for use in the treatment of industrial wastes. The polymers are produced, however, by the treatment of corresponding nitrile polymers and are therefore governed by the structure of the nitrile polymers. Furthermore, conversion of the nitrile polymers to the imidazoline or amidine form does not reach 100% and therefore a portion of the resultant polymer is in improper form to function in water treating capacity.

Prior attempts to obviate these difficulties have included rearrangement of the groups present in the nitrile charge polymer and the attempted production of unsaturated imidazolines and amidines which may be homopolymerized or copolymerized into more active imidazoline and amidine polymers. However, attempts to produce intermediates, from which the unsaturated imidazolines and amidines may be prepared, have proven unsuccessful. Furthermore, attempts to follow the teachings of U.S. Pat. No. 3,210,371 resulted only in the production of undesired polymeric material and the teachings of Oxley et al., J. Chem. Soc. 1947, pages 497–505, also resulted in the recovery of undesired polyermic products.

Recent developments are typified by U.S. Pat. Nos. 4,006,247 and 4,007,200. In U.S. Pat. 4,007,200, there are disclosed intermediates which require numerous preparative steps which are difficult to perform thus complicating processing and reducing yields of the intermediate. In U.S. Pat. No. 4,006,247, it is disclosed that the intermediates of U.S. Pat. No. 4,007,200 can be cracked to provide unsaturated imidazolines and amidines. However, the intermediate is unstable in cracking thus reducing yields of unsaturated compounds. The cracking process is difficult to perform and undesirable.

There continues to exist the need for improved intermediates for unsaturated imidazolines and amidines which are readily prepared and are easily converted to the desired unsaturated compounds by simple processing. Such a provision would fulfill a long-felt need and constitute a notable advance in the art.

In accordance with the present invention, there are provided compounds of the structure

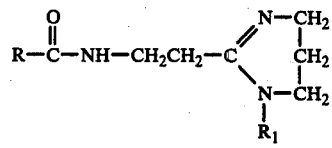

wherein R is an alkyl group of about 1 to 5 carbon atoms and $R_1$ is hydrogen or an alkyl group of about 1 to 5 carbon atoms.

Compounds of the present invention are stable intermediates which are readily prepared and are readily cleaved to provide vinyltetrahydropyrimidines. Their ready processability results in savings in materials, processing steps, and processing costs while providing good yields of monomeric product which can be readily processed to the desired polymers for the various uses previously mentioned.

As indicated, the compounds of the present invention have the structure

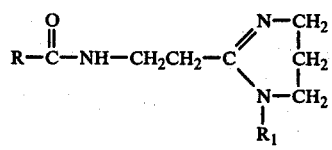

wherein R is an alkyl group of about 1 to 5 carbon atoms and $R_1$ is hydrogen or an alkyl of about 1 to 5 carbons. When the compounds are cleaved, an acylamide is provided as well as the vinylpyrimidine. It is desirable that the acylamide have a higher boiling point than the vinylpyrimidine so as to provide easier separation of these cleavage products. Typical compounds of the present invention are 2-acetamidoethyl-2-tetrahydropyrimidine, 2-propionamidoethyl-2-tetrahydropyrimidine, 2-propionamidoethyl-2-(1-methyl)tetrahydropyrimidine, 2-butryamidoethyl-2-tetrahydropyrimidine, and the like.

The compounds of the present invention, which are 2-acylamidoethyl-2-tetrahydropyrimidines, are conveniently prepared starting with a suitable 2-cyanoethylacylamide. This starting compound type is known in the art and is readily prepared by reacting acrylonitrile with an acylamide in the presence of a strong alkali. The reaction is described in the Chemistry of Acrylonitrile, IV Cyanoethylation of Active Hydrogen Groups, Bruson and Riener, J. Am. Chem. Soc., 65, page 23 (1943). This reaction is given by the equation

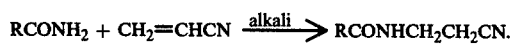

For the purposes of the present invention, R is an alkyl group of about 1 to 5 carbon atoms.

Using a selected 2-cyanoethylacylamide as described, the desired 2-acylamidoethyl-2-pyrimidine of the present invention is prepared by reaction thereof with a propylenediamine of the structure $R_1HN-CH_2CH_2CH_2-NH_2$, wherein $R_1$ is hydrogen or an alkyl group of about 1 to 5 carbon atoms, preferably in the presence of a suitable catalyst. A preferred catalyst is sulfur. The reaction is carried out at en elevated temperature to minimize reaction time but at a temperature safely below that at which decomposition occurs. Reaction is quite rapid, generally 90 minutes or less at 115° C. A solvent may be used if desired but reaction can be effected in the absence of solvent. The crude product obtained is readily purified by recrystallization, for example, and yields of pure product are 70% or higher. The reaction follows the equation

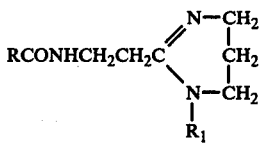

The reactants are generally used in equal molar amounts. If a catalyst is employed, it is used in an effective amount. Preferably, sulfur is used at a concentration of about 0.5 to 1.0 weight percent based on the weight of reactants. As indicated, a solvent may be used if desired and, if used, should generally be in an amount providing suitable fluidity to the reaction mixture. A preferred solvent is toluene.

The compounds of the present invention are readily cleaved to provide the desired vinylpyrimidine monomer. Cleavage can be effected by heating the intermediate in the presence of suitable cracking agents in a reaction flask and distilling off and recovering the cleavage products. Separation of the vinylpyrimidine monomer by suitable procedure, such as by preparing a salt of the vinylpyrimidine. The cleavage reaction which forms the desired vinylpyrimidine monomer, is given by the equation

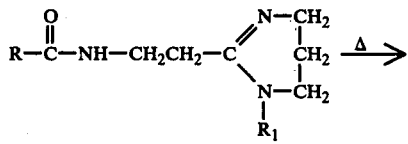

-continued

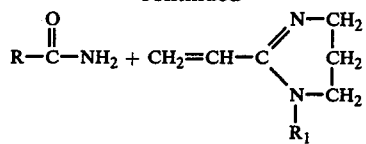

wherein R and $R_1$ have the meaning previously given.

The invention is more fully illustrated by the examples which follow wherein all parts and percentages are by weight unless otherwise specified.

EXAMPLE 1

Preparation of 2-Acetamidoethyl-2-tetrahydropyrimidine

To a 500 ml round-bottomed flask equipped with a thermometer and reflux condenser were added 129.00 grams (1.15 mol) of 2-cyanoethylacetamide, 83.62 grams (1.13 mol) of 1,3-diaminopropane, 1.5 grams of sulfur and 100 ml. of toluene as solvent. The reaction mixture was heated to 110° C. and held at this temperature for 3 hours. A solid product precipitated upon cooling in the amount of 186 grams. Upon recrystallization of the crude product from ethyletherethanol (150 ml. 1:3), 149 grams of pure product was recovered representing a yield of 78.5%. The product had a melting point of 165–167° C.

EXAMPLE 2

To a 250 ml. round-bottomed flask equipped with a distillation head, vacuum take-off adapter, and a receiver were added 22.2 grams (0.144 mol) of 2-acetamidoethyl-2-tetrahydropyrimidine as obtained in Example 1, 11.5 grams of Celite, 4.0 grams of potassium hydroxide, 4.8 milligrams of Cupferon, and 0.5 grams of phenothiazine. The mixture was thoroughly mixed and heated to 200° C. at a pressure equivalent to 0–5 millimeters of mercury. The yield of 2-vinyl-2-tetrahydropyrimidine was 50% based on NMR.

EXAMPLES 3-6

Following the procedure of Example 1 in every material detail, a series of preparations were made. In each preparation an equivalent molar amount of 2-cyanoethylacylamide and a propylenediamine were used in place of that used in Example 1. In each instance, a corresponding 2-acylamidoethyl-2-tetrahydropyrimidine was obtained in good yield and having a structure consistent with the desired product. The 2-acylamidoethyl-2-tetrahydropyrimidines were cleaved to the corresponding 2-vinyl-2-tetrahydropyrimidines following the procedure of Example 2. The reactants and products obtained are given below along with the example number.

| Example No. | 2-cyanoethyl acylamide(R-group) | Propylene Diamine($R_1$-group) | Product |
|---|---|---|---|
| 3 | $C_2H_5-$ | H— | ![structure] $C_2H_5CONHCH_2CH_2-C$ with N—CH$_2$, CH$_2$, N—CH$_2$, H ring |

-continued

| Example No. | 2-cyanoethyl acylamide(R-group) | Propylene Diamine($R_1$-group) | Product |
|---|---|---|---|
| 4 | $C_3H_7-$ | $CH_3-$ | $C_3H_7CONHCH_2CH_2-C\underset{\underset{CH_3}{N}-CH_2}{\overset{N=CH_2}{<}}\begin{smallmatrix}CH_2\\CH_2\end{smallmatrix}$ |
| 5 | $C_2H_5-$ | $C_2H_5-$ | $C_2H_5CONHCH_2CH_2-C\underset{\underset{C_2H_5}{N}-CH_2}{\overset{N=CH_2}{<}}\begin{smallmatrix}CH_2\\CH_2\end{smallmatrix}$ |
| 6 | $CH_3-$ | $C_3H_7$ | $CH_3CONHCH_2CH_2-C\underset{\underset{C_3H_7}{N}-CH_2}{\overset{N=CH_2}{<}}\begin{smallmatrix}CH_2\\CH_2\end{smallmatrix}$ |

We claim:
1. A compound of the structure

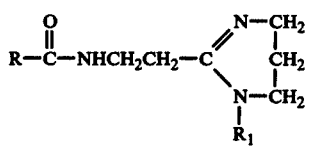

wherein R is an alkyl group of 1 to 5 carbon atoms and $R_1$ is hydrogen or an alkyl group of 1 to 5 carbon atoms.

2. A compound of claim 1 wherein R is methyl and $R_1$ is hydrogen.

3. A compound of claim 1 wherein R is ethyl and $R_1$ is hydrogen.

4. A compound of claim 1 wherein R is propyl and $R_1$ is methyl.

5. A compound of claim 1 wherein R is ethyl and $R_1$ is ethyl.

* * * * *